United States Patent
Bornzin et al.

(10) Patent No.: US 7,454,249 B1
(45) Date of Patent: Nov. 18, 2008

(54) EARLY WARNING FOR LEAD INSULATION FAILURE

(75) Inventors: Gene A. Bornzin, Simi Valley, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 399 days.

(21) Appl. No.: 11/174,395

(22) Filed: Jun. 30, 2005

(51) Int. Cl.
*A61N 1/37* (2006.01)
(52) U.S. Cl. .......................................... 607/27; 607/28
(58) Field of Classification Search ............. 607/27–29, 607/116, 119
See application file for complete search history.

(56) References Cited

U.S. PATENT DOCUMENTS

| | | | |
|---|---|---|---|
| 4,320,764 A * | 3/1982 | Hon | 600/351 |
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 5,466,254 A | 11/1995 | Helland | 607/123 |
| 5,476,483 A | 12/1995 | Bornzin et al. | 607/17 |
| 5,507,786 A | 4/1996 | Morgan et al. | 607/27 |
| 5,755,742 A | 5/1998 | Schuelke et al. | 607/27 |
| 5,837,900 A | 11/1998 | Lipson | 73/661 |
| 5,897,577 A | 4/1999 | Cinbis et al. | 607/28 |
| 6,314,323 B1 | 11/2001 | Ekwall | 607/23 |
| 6,862,475 B1 * | 3/2005 | Kroll | 607/9 |

FOREIGN PATENT DOCUMENTS

| | | |
|---|---|---|
| EP | 0944413 B1 | 2/2001 |
| WO | WO 98/19738 | 5/1998 |
| WO | WO 99/24113 | 5/1999 |

OTHER PUBLICATIONS

Dorwarth, Uwe MD et al., "Transvenous Defibrillation Leads: High Incidence of Failure During Long-Term Follow-up," J. Cardivasc Electrophysiol, vol. 14, pp. 38-43, Jan. 2003.

* cited by examiner

*Primary Examiner*—Carl H Layno
*Assistant Examiner*—Eugene T Wu

(57) ABSTRACT

An exemplary implantable device includes a microcontroller programmed to control delivery of cardiac therapy, a connector capable of making an electrical connection to an insulated conductor associated with an exposed electrode and a circuit connected to the conductor to measure an electrical half-cell potential of the electrode via the conductor and to signal the microcontroller if a defect occurs with respect to the insulated conductor. Such a defect may be an insulation defect and/or a conductor defect. Other exemplary methods, devices, systems, etc., are also disclosed.

12 Claims, 11 Drawing Sheets

EXEMPLARY DISSIMILAR
MATERIAL POTENTIAL
600

Exemplary Circuit

EARLY WARNING FOR LEAD INSULATION FAILURE

TECHNICAL FIELD

Subject matter presented herein generally relates to cardiac pacing, cardiac shock, sensing and/or stimulation therapies. Various exemplary methods, devices, systems, etc., concern condition of leads used for pacing, shock, sensing and/or stimulation.

BACKGROUND

Various studies indicate that an implanted lead may fail for one or more reasons. For example, a study by Dorwarth et al., "Transvenous defibrillation leads: high incidence of failure during long-term follow-up", *J Cardiovasc Electrophysiol.*, 14(1):38-43 (2003), found that a majority of lead-related sensing failures were associated with insulation defects that occurred late after ICD placement (6.0+/−1.8 years after implant). Dorwarth et al. recognized that "automated device control features with patient alert function integrated into new devices may contribute to early detection of lead failure". Thus, a need exists for techniques to detect lead failure.

To date such techniques typically rely heavily on impedance measurement. An excessive lead impedance may indicate loss of a connection due to a conductor fracture and a low lead impedance may indicate a short circuit or alternative conduction path due to an insulation failure. While impedance techniques offer some benefits, they also have some possible disadvantages. For example, a possible disadvantage relates to power consumption in that many impedance techniques rely on use of an applied voltage. Further, impedance techniques may be inadequate for detection of a low impedance insulation failure or defect that could compromise a high energy defibrillation shock or compromise device operation. Various exemplary methods, devices, systems, etc., disclosed herein aim to address lead issues and/or other issues.

SUMMARY

An exemplary implantable device includes a microcontroller programmed to control delivery of cardiac therapy, a connector capable of making an electrical connection to an insulated conductor associated with an exposed electrode and a circuit connected to the conductor to measure an electrical half-cell potential of the electrode via the conductor and to signal the microcontroller if a defect occurs with respect to the insulated conductor. Such a defect may be an insulation defect and/or a conductor defect. Other exemplary methods, devices, systems, etc., are also disclosed.

In general, the various exemplary methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart. Various techniques may be implemented in connection with any stimulation, sensing and/or other device that relies on implantation of at least two dissimilar metals (e.g., metals, alloys, etc.) in a body and/or in contact with conductive body tissue, fluid, etc.

Figure 1:
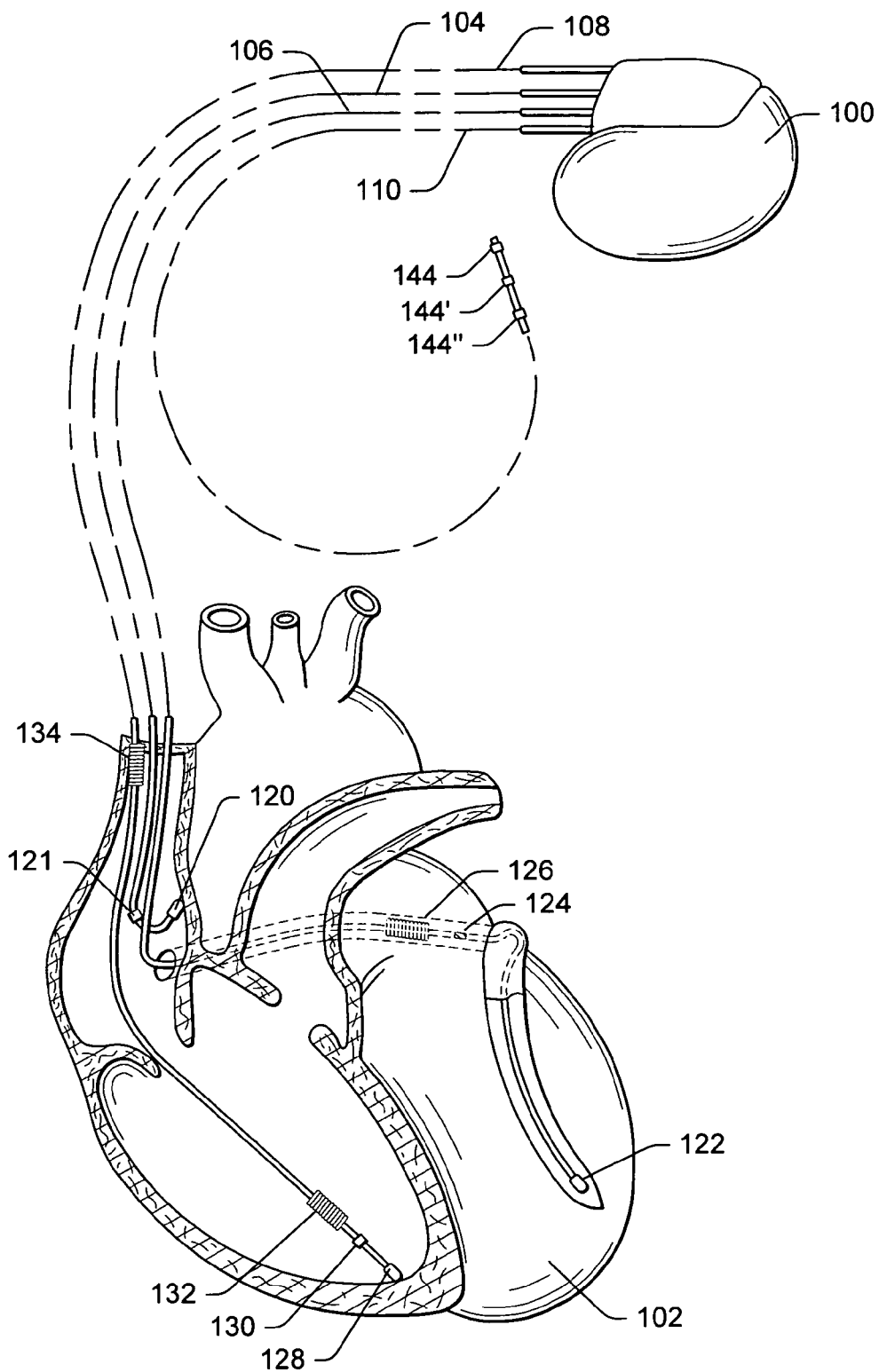
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
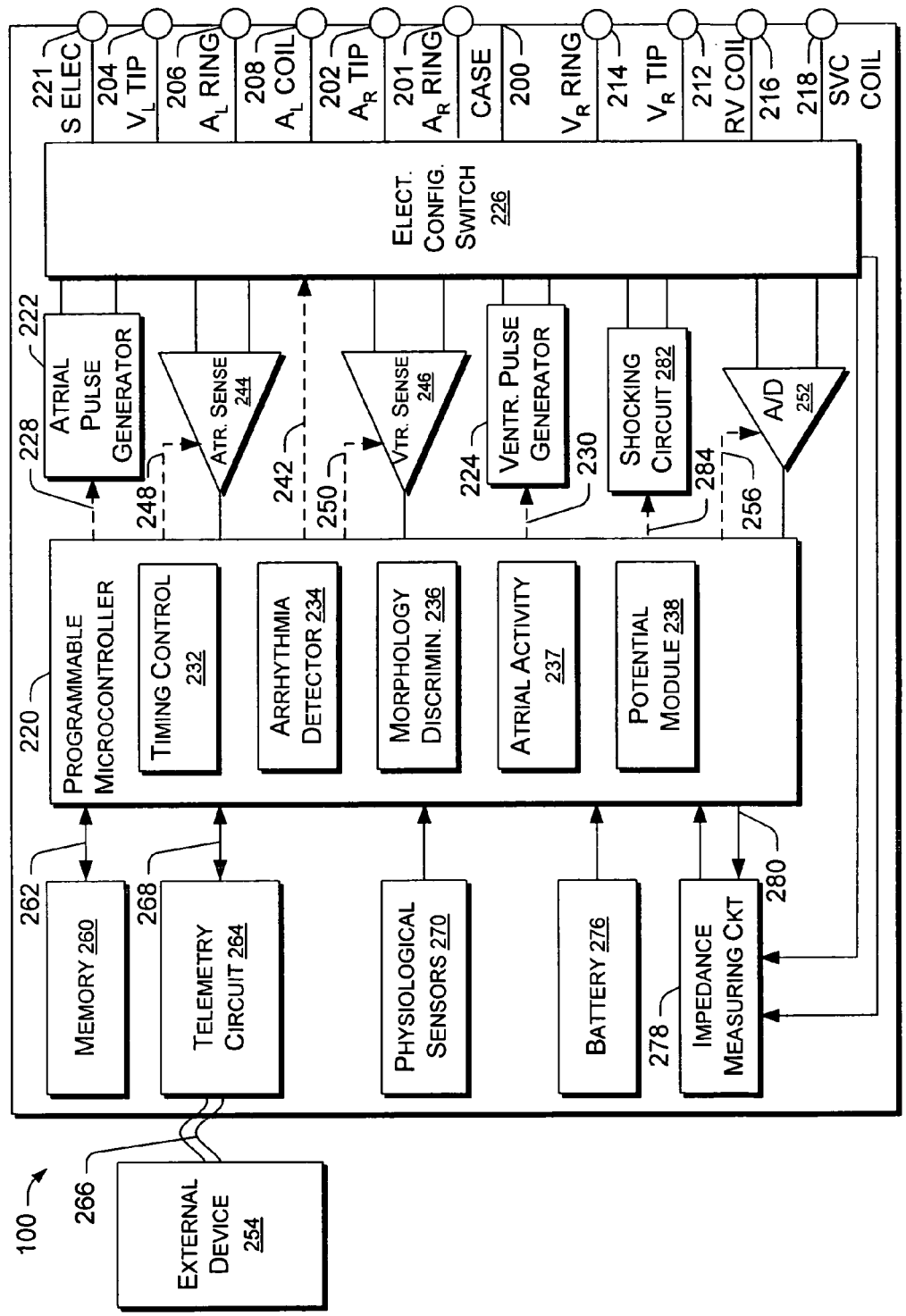
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administers stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity.

Microcontroller 220 further includes a potential module 238 for performing a variety of tasks related to, for example, one or more half-cell potentials. This component can be utilized by the stimulation device 100 in determining therapy in response to condition of insulation and/or a conductor associated with an electrode. The potential module 238 may be implemented in hardware as part of the microcontroller 220, or as software/firmware instructions programmed into the device and executed on the microcontroller 220 during certain modes of operation. The potential module 238 may optionally implement various exemplary methods described herein.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5

J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Exemplary Implant Arrangement

Figure 3:
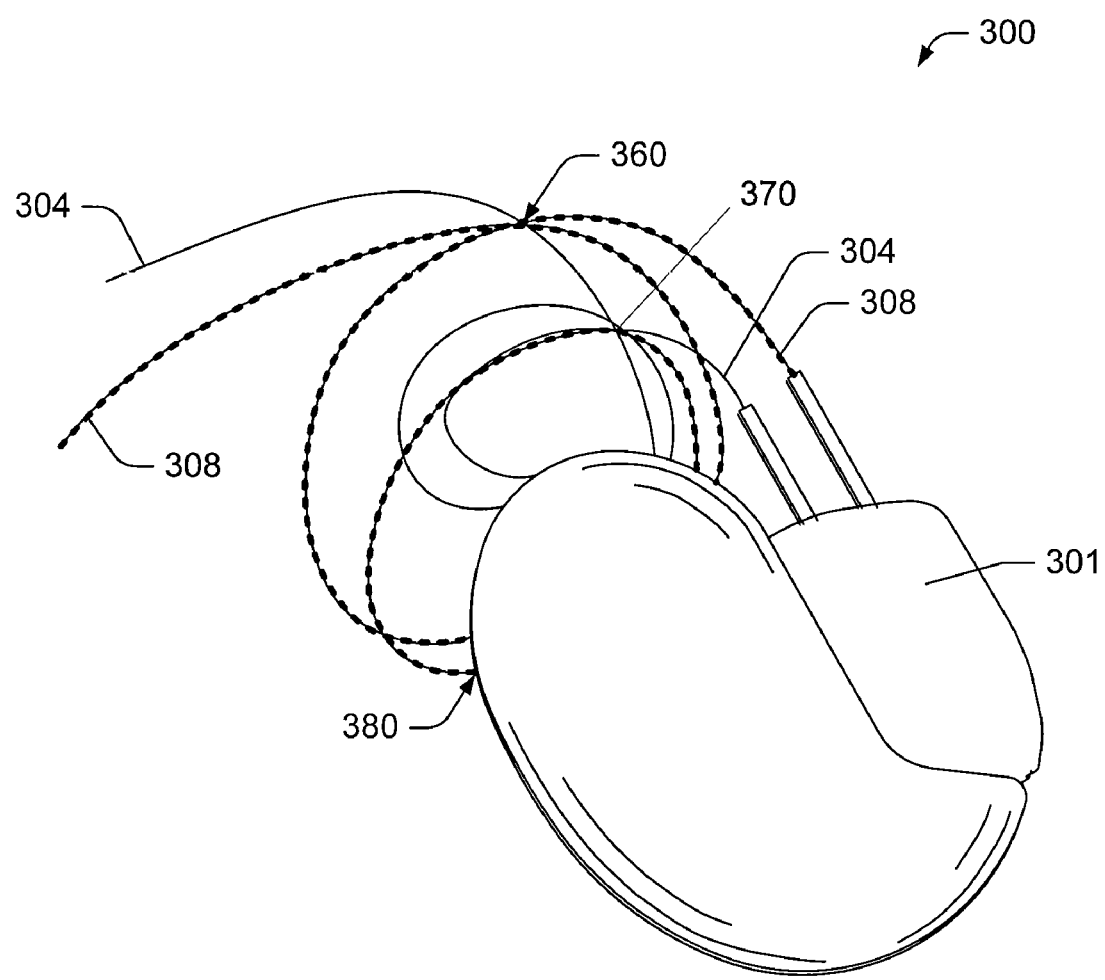
FIG. 3 is a diagram of an exemplary implantable device that includes two leads that are looped and in proximity (e.g., possible contact) with the case of the implantable device.

FIG. 3 shows an exemplary implant arrangement 300 that includes an exemplary device 301 and two leads 304, 308. Implanted cardiac pacing, sensing and/or shock devices are typically positioned subcutaneously in a left pectoral pocket. Implanted devices for deep brain stimulation may also be positioned in a pectoral or other pocket. In either instance, actual lead length typically exceeds needed lead length. As such, upon implantation, one or more leads may be looped and positioned proximate to or in the device's pocket. X-ray images of implanted cardiac stimulation devices appear in various journals and serve to illustrate such looping.

In FIG. 3, the leads 304, 308 each loop twice before extending to the left side of the figure and represent a typically implant arrangement. As the leads 304, 308 loop, they may self-contact 360, contact each other 370 and/or contact the device 380. In other instances, one or more of the leads may contact bone or other hard tissue. All of these forms of contact may cause, typically over an extended time, lead insulation defects or failures. Various exemplary methods, devices and/or systems aim to detect such defects and/or failures.

Figure 4:
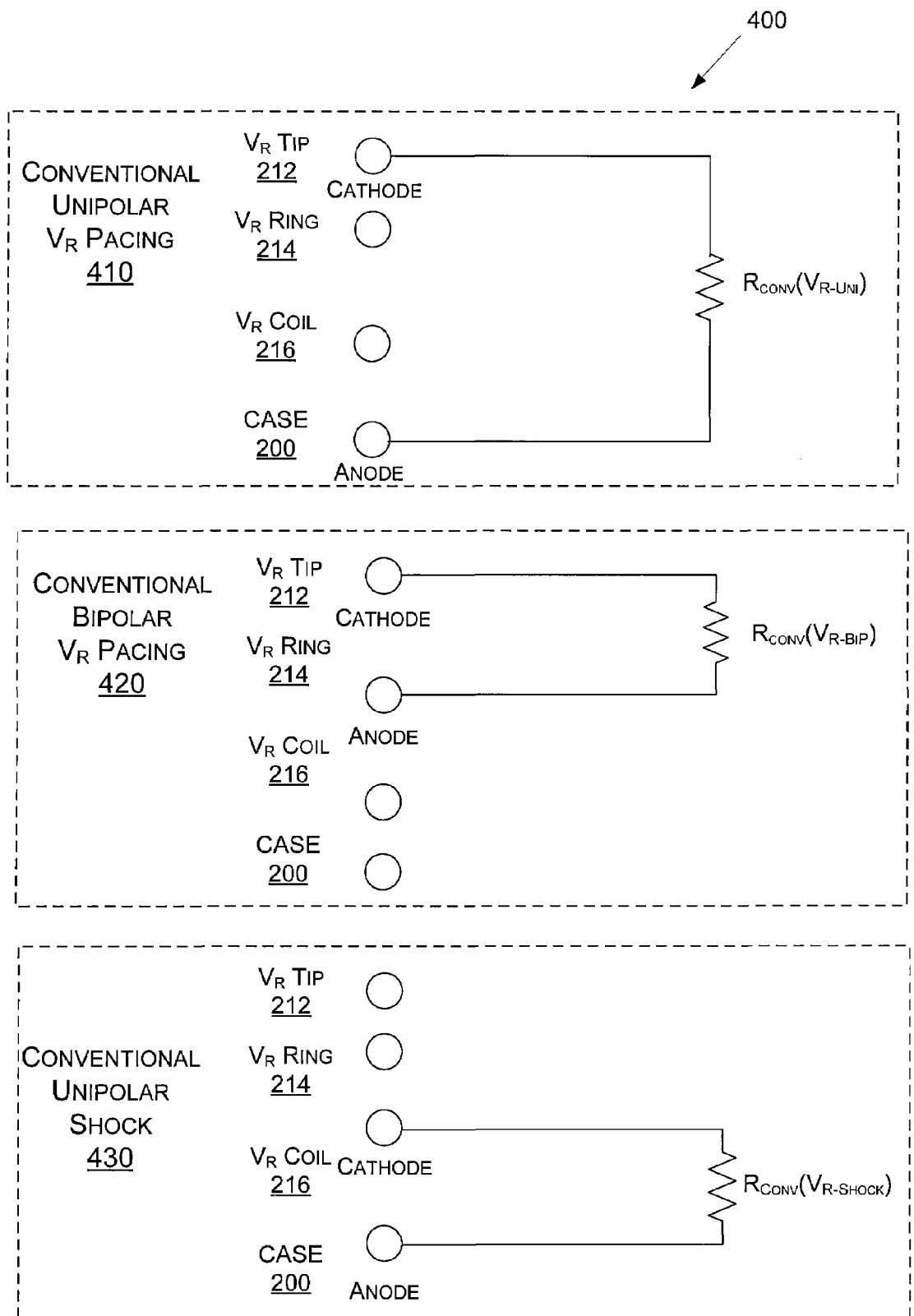
FIG. 4 is a diagram of various conventional pacing and/or shocking arrangements wherein a current path having a certain resistance exists in the body.

To understand better various techniques, FIG. 4 shows various examples of conventional lead and electrode configurations 400. The configuration 410 represents a conventional unipolar right ventricular pacing configuration that includes use of a cathodic right ventricular tip electrode on a right ventricular lead connected at a connector 212 and an anodic case electrode at a connector 200. A corresponding resistance, $R_{Conv}(V_{R-Uni})$, represents a resistance between the two electrodes. As discussed herein, and elsewhere, a change in such a resistance may indicate the existence of a lead, electrode, tissue or other issue. The configuration 420 represents a conventional bipolar right ventricular pacing configuration that includes use of a cathodic right ventricular tip electrode on a right ventricular lead connected at a connector 212 and an anodic right ventricular ring electrode at a connector 214. A corresponding resistance, $R_{Conv}(V_{R-BiP})$, represents a resistance between the two electrodes. As discussed herein, and elsewhere, a change in such a resistance may indicate the existence of a lead, electrode, tissue or other issue. The configuration 430 represents a conventional unipolar shock configuration that includes use of a cathodic right ventricular coil electrode on a right ventricular lead connected to a connector 216 and an anodic case electrode at a connector 200. A corresponding resistance, $R_{Conv}(V_{R-Shock})$, represents a resistance between the two electrodes. As discussed herein, and elsewhere, a change in such a resistance may indicate the existence of a lead, electrode, tissue or other issue.

Figure 5:
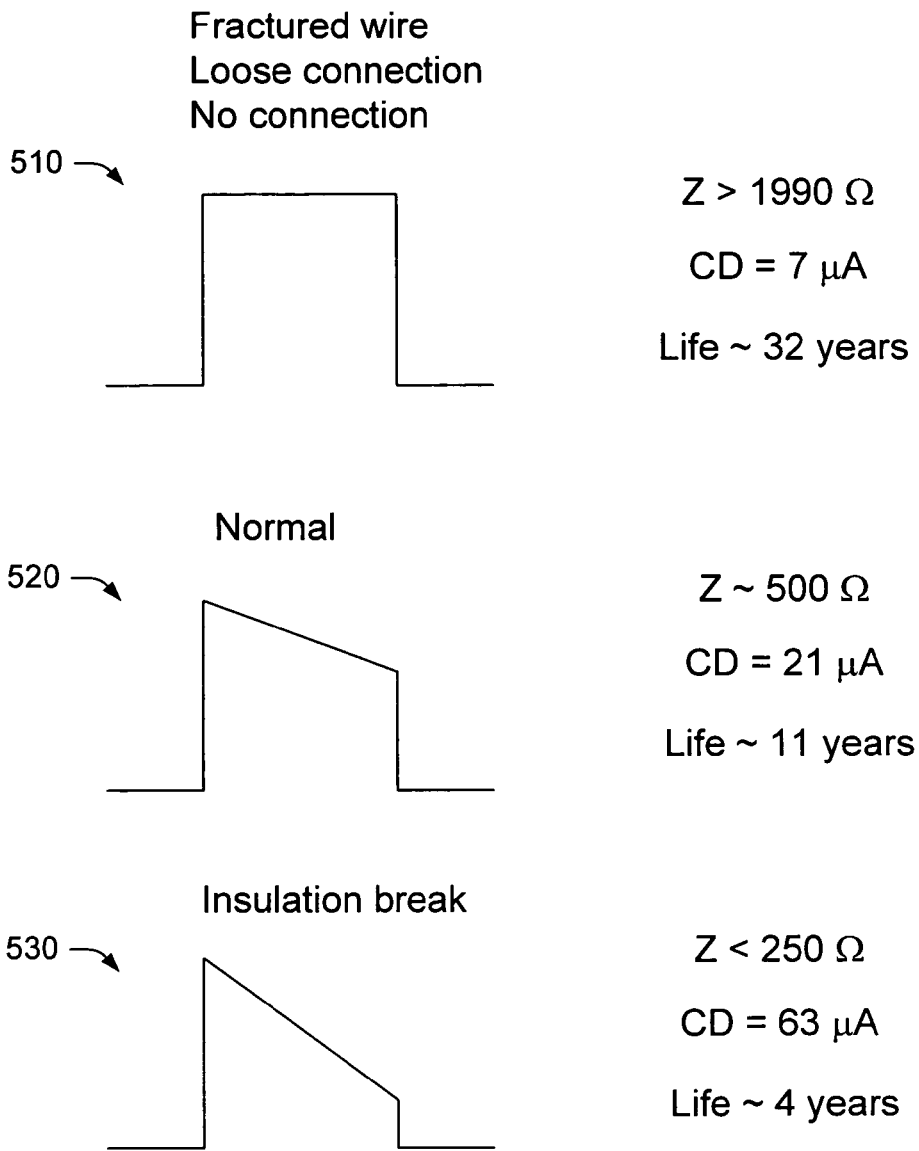
FIG. 5 is a diagram that includes a plot corresponding to a conduction issue, a plot corresponding to a normal situation and a plot corresponding to an insulation failure.

In general, the impedance of a lead depends on the end electrodes which are typically designed to have a high impedance value. The lead conductor is designed to have a low impedance value and to be insulated from the body. However, if the insulation fails then a low impedance value lead conductor is exposed to the tissue and the impedance will drop in this circuit. FIG. 5 shows various scenarios 500 associated with leads. A first scenario 510 has an electrode impedance value that exceeds approximately 1990Ω. In the scenario 510, current drain from an associated and typical cardiac stimulation device is minimal and less than 10 μA. While the scenario 510 is not desirable, the battery life would be quite long, for example, greater than about 30 years. Thus, a scenario that involves a fractured wire, a loose connection, and/or no connection may be associated with a low current drain and high impedance. If an insulation failure were to occur intermediate a potential sensing circuit and the point where a fractured wire, a loose connection, and/or no connection occurs, then the potential sensing circuit may indicate any such insulation failure. A second scenario 520 represents a normal situation having an electrode impedance of approximately 500Ω (e.g., a pacing electrode), a current drain of approximate 21 μA and a battery life of about 11 years (e.g., drain potential of about 11 mV). In general, normal impedance ranges from about 300Ω to about 1500Ω for cardiac pacing electrodes. A third scenario 530 has an electrode impedance less than about 250Ω, a current drain of about 63 μA and a shortened battery life of about 4 years. The scenario 530 is undesirable for at least several reasons. First, the increase in current drain can shorten battery life dramatically and, second, an insulation break typically exposes at least a portion of a lead conductor and thus creates secondary current paths.

With respect to low energy stimuli and/or sensing, insulation defects such as those associated with the scenario 530 may cause inappropriate stimulation and/or inappropriate sensing. Inappropriate stimulation may fail to stimulate target tissue and/or cause an increase in stimulation energy while inappropriate sensing may cause an implanted device to implement inappropriate therapy and/or report incorrect data. With respect to higher energy stimulation or shock, an insulation defect or failure may have catastrophic consequences. For example, if the lead 308 of FIG. 3 has an insulation failure adjacent to the case of the device 301, a high energy pulse delivered via the lead 308 may cause arc welding of a lead conductor to the case of the device 301. In general, if friction between a lead and a case causes an insulation defect, then a high likelihood exists for contact or a short circuit between a conductor of the lead and the case.

For biventricular systems or other arrangements where multiple leads may have one or more common electrical connections, may not exhibit behavior exactly like that of the scenarios of FIG. 5. For example, in a biventricular output configuration, lead impedance may be around 250Ω to about 400Ω with proper lead and insulation integrity. An open in one lead (e.g., a conductor fracture) having a common with another lead will not result in a high impedance value as for scenario 510. Instead, the biventricular system will have an increased impedance value, for example, to about 500Ω to about 750Ω. However, where circuitry is available to measure impedance of leads and/or electrodes individually, the scenarios of FIG. 5 may be instructive.

Figure 6:
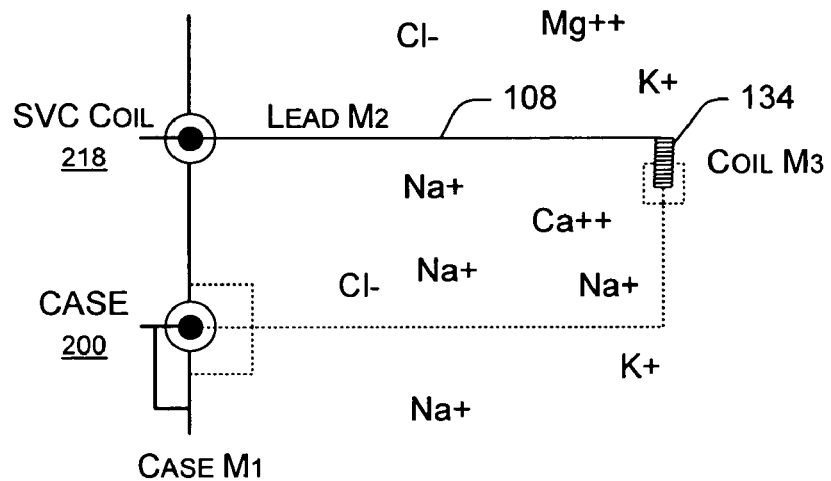
FIG. 6 is diagram of an exemplary mechanism for detecting insulation and/or other issues and an implementation of the mechanism as applied to a coil electrode in contact with a conductive solution or tissue and a case electrode in contact with a conductive solution or tissue wherein the two electrodes are of dissimilar materials of construction, at least as exposed to the conductive solution(s) or tissues.

FIG. 6 shows an exemplary mechanism and implementation thereof 600 for detecting condition of insulation, a metal, an alloy, etc. and includes three metals or alloys (M1, M2, M3), insulation and a conductive solution. A conductive tissue may substitute or be used in addition to the conductive solution. Various potentials exist between M1, M2 and/or M3 based on electrical potentials of M1, M2, M3 and properties of the conductive solution. For example, platinum is more noble or less susceptible to corrosion than titanium, also consider that a difference in half-cell potential exists between titanium and titanium nitride. Taking into consideration spontaneous formation of passivating layers (e.g., oxide layers, etc.), platinum in salt water has an electrical potential of approximately −1.5 V and titanium in salt water has an electrical potential of approximately −0.47 V. Thus, according to these values, a potential of about +/−1 V exists between platinum and titanium in salt water (sodium chloride). If M1 is titanium, M3 is platinum and the conductive solution is a saline representative of a general body fluid (~1% NaCl salt plus other ions in water), then a potential exists between M1 and M3. This potential may be measured by placing a probe in contact with M1 and another probe in contact with M3. Should the insulation fail, then M2 may contact the conductive solution and hence enter into the analysis. In general, failure of the insulation will expose M2 and thereby cause a change in the potential as measured between M1 and M3. Accordingly, this exemplary mechanism allows for detecting condition of the metals or alloys and/or the insulation. Further, while a break in M2 may cause a measurement to fail, it should not significantly alter the actual potential between M1 and M3, assuming the insulation does not fail.

In a second embodiment a coil composed of metal or alloy M3 connects to a SVC connector 218 via an insulated lead conductor composed of metal or alloy M2. A case connector 200 connects to a case of an implanted device composed of metal or alloy M1, where M1 differs from M3 to at least some extent. A dashed line represents a current path upon delivery of a shock using a unipolar electrode configuration that includes the coil and the case.

As shown, the case and the coil contact a conductive solution that includes ions such as Na+, K+, Mg++, Ca++, Cl−, etc. Consequently, electrical potentials exist for the coil and the case with respect to the conductive solution. Further, where M1 and M3 differ, a potential difference exists between the coil and the case. This potential difference may be measured using circuitry in the case of the device that can form a circuit with the coil connector 218 and the case 200. Using such circuitry, a failure in the insulation of the lead 108 may cause the conductor to the coil 134 to become exposed to the conductive solution and thereby alter the measured potential. If the failure in the insulation of the lead 108 causes the conductor of the coil 134 to come into contact with the case 200, then a short occurs whereby the measured potential will change. If a break occurs in the conductor to the coil 134, then the measured potential should also change, typically in a manner that differs from the two aforementioned insulation related situations.

Accordingly, an exemplary method may determine a potential difference between a first half-cell potential associated with a first electrode composed of a first material in contact with a conductive fluid or tissue and a second half-cell potential associated with a second electrode composed of a second material in contact with a conductive fluid or tissue and alter a cardiac therapy if the difference falls below a predetermined limit or does not compare favorably to one or more limits. The cardiac therapy may be related to sensing, stimulation, shock, etc. Of course, an exemplary method may apply to a non-cardiac therapy, such as, neurostimulation (e.g., nerve and/or brain tissue stimulation), muscle stimulation, drug delivery, etc.

As mentioned above for a biventricular system or other system, an exemplary method, device, system, etc., may account for potentials wherein a common exists between more than one lead and/or electrode. Where circuitry is available to measure impedance of leads and/or electrodes individually, with a common electrode (e.g., case), etc., then such circuitry may be used for such systems.

Figure 7A:
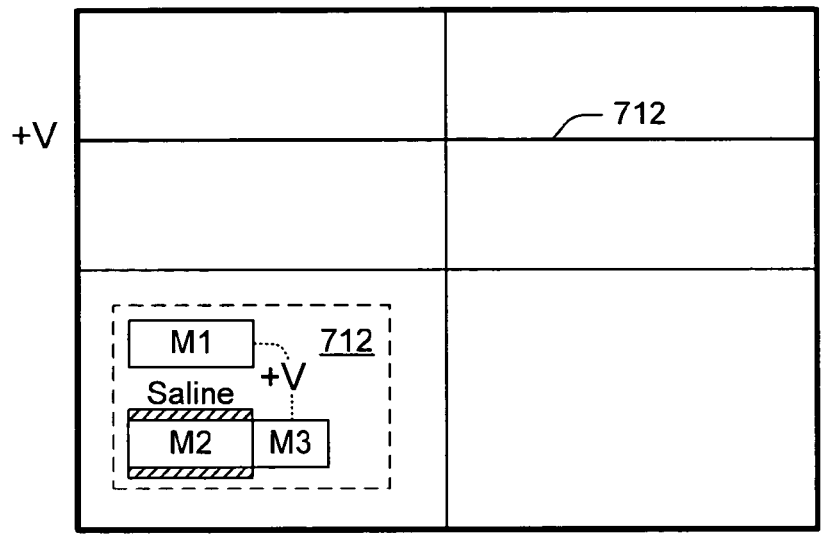
FIG. 7A is a diagram that includes two plots of potential difference versus time as measured using a device, electrodes and a conductive solution.
Figure 7A:
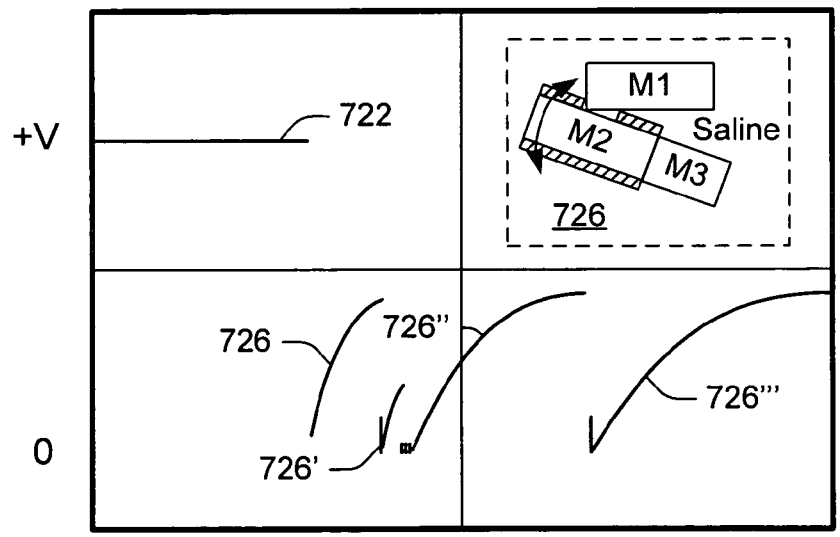

FIG. 7A shows several exemplary plots of potential difference versus time. A first plot 710 corresponds to a normal scenario where a relatively constant potential 712 exists between a coil electrode and a case of an implantable device wherein the coil electrode and the case of the device are in contact with a conductive solution. A second plot 720 corresponds to a series of events associated with a failure in insulation of a conductor to the coil electrode. In this scenario, each event 726, 726', 726", 726'" causes the potential difference to decrease from a normal value 722 to a low value as the conductor contacts the case. Each of the events 726, 726', 726", 726'" may represent contact between the case and the conductor to the coil electrode wherein the low value corresponds to actual contact. After each of the events 726, 726', 726", 726'", the potential difference changes in an exponential manner to a relatively constant value. In general, the time constants of such behavior can be differentiated from time constants associated with other conditions that could give rise to such changes in potential.

Figure 7B:
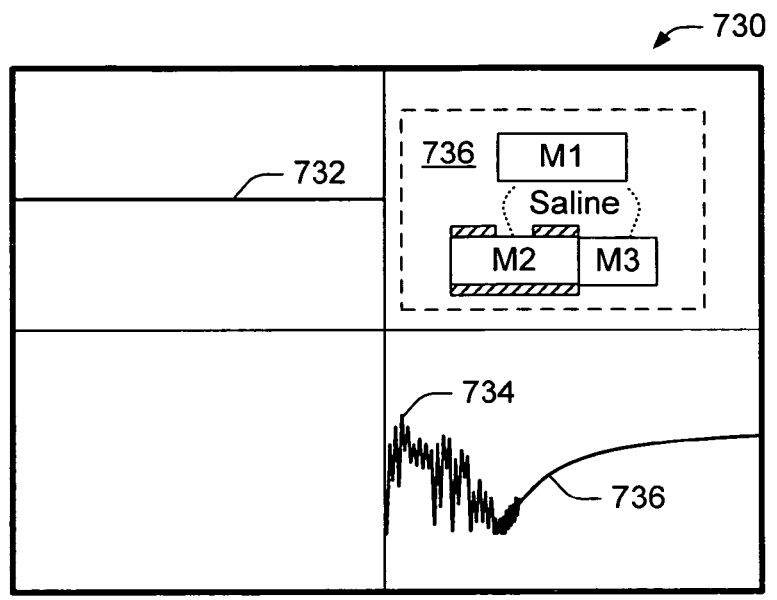
FIG. 7B is a diagram that includes two plots of potential difference versus time as measured using a device, electrodes and a conductive solution.
Figure 7B:
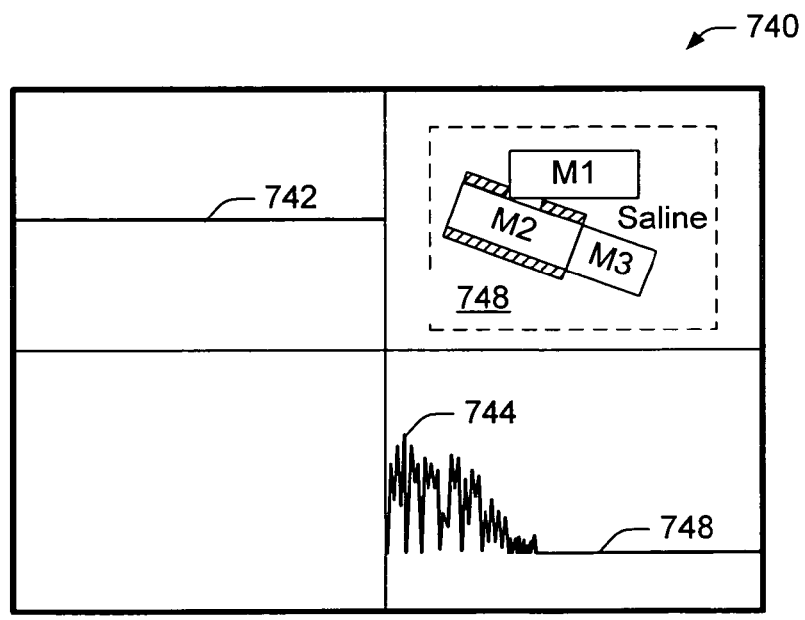

FIG. 7B shows several additional exemplary plots of potential difference versus time. A first plot 730 corresponds to a normal potential difference 732 followed by a series of failure events 734 followed by a contact event 736 that rises to a relatively constant value that differs from the normal value 732. The relatively constant value following the rise after the contact event 736 may correspond to introduction of a third potential between the conductor metal or alloy (e.g., M2) and the conductive solution that affects the potential difference between the metal or alloy M1 and M3, as measured. A second plot 740 corresponds to a normal potential difference 742 followed by a series of failure events 744 followed by a prolonged contact event 748 between the conductor of the coil (e.g., M2) and the case (e.g., M1).

While the exemplary plots 710, 720, 730, 740 exhibit behaviors associated with various insulation-related scenarios, other behaviors may be observed and associated with same or other scenarios. Overall, the exemplary mechanism described with reference to FIG. 6 allows for detection of changes that may occur with respect to insulation and/or one or more metals in a conductive solution. For example, formation of a passivation layer (e.g., oxidation layer), degradation of a coating, wetting by a conductive solution, bubble formation at a surface, etc., can alter a measurable potential and/or a measurable potential difference.

Figure 8:
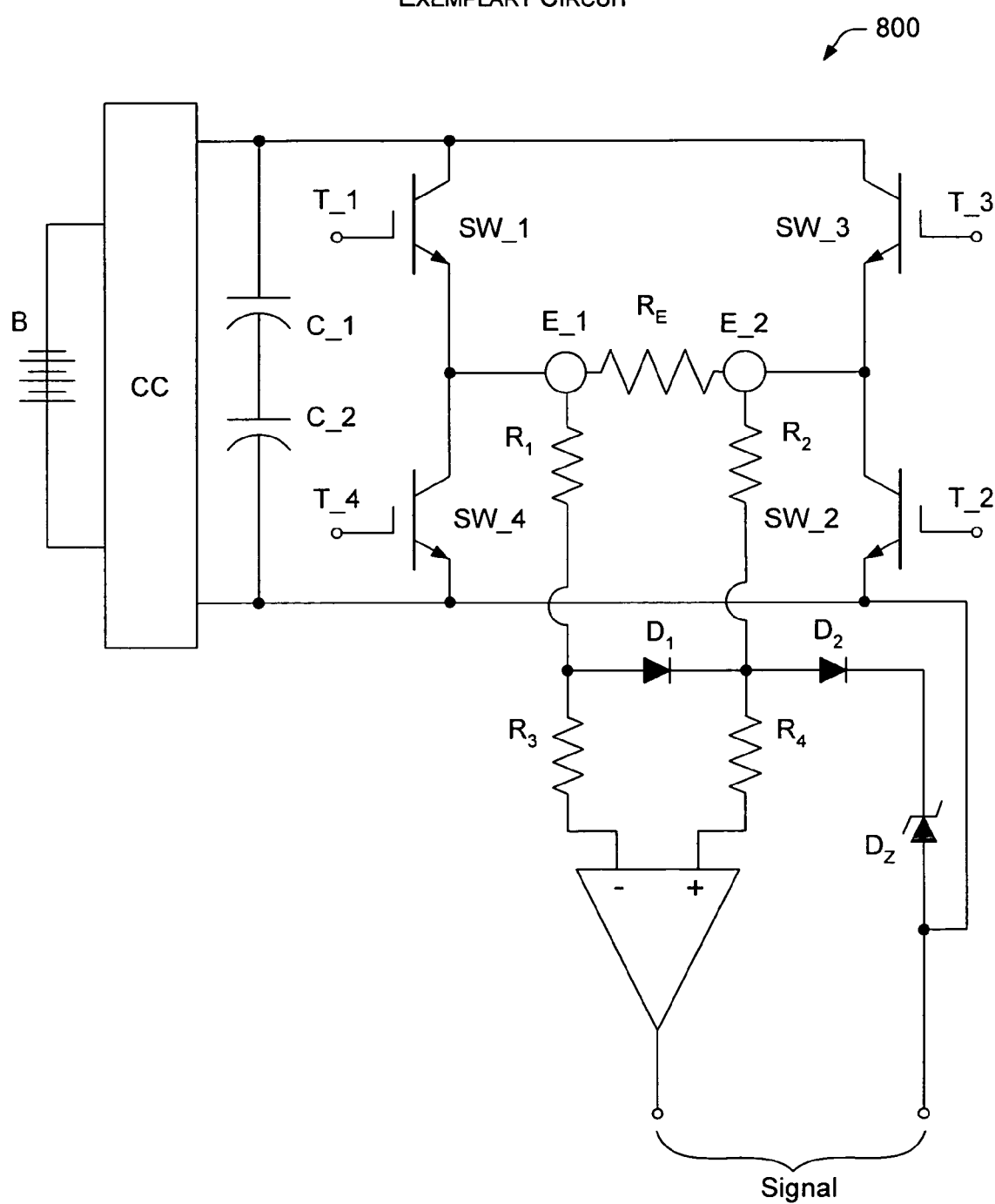
FIG. 8 is a schematic of an exemplary circuit capable of measuring one or more electrical potentials.

FIG. 8 shows an exemplary circuit 800 suitable for use in measuring a potential difference between two electrical potentials. The circuit 800 includes a battery (B) and a charging circuit (CC) capable of using energy stored in the battery to charge a first capacitor (C_1) and a second capacitor (C_2). The two capacitors (C_1, C_2) are electrically connected to an H-bridge that can control discharge of the capacitors. The H-bridge includes four switches (SW_1, SW_2, SW_3, SW_4) and corresponding switch triggers (T_1, T_2, T_3, T_4). The switches and triggers allow for delivery of, for example, a biphasic shock via two electrodes (E_1, E_2) across a resistance (RE), wherein a first phase corresponds to triggering switches SW_1 and SW_2 and a second phase corresponds to triggering switches SW_3 and SW_4.

As mentioned, an exemplary mechanism involves measuring one or more electrical potentials and/or a potential difference. A potential difference measurement circuit includes electrical connections to the electrodes E_1 and E_2. As shown in the exemplary circuit 800, the electrode E_1 connects to a DC amplifier via a resistors $R_1$ and $R_3$ and the electrode E_2 connects to the DC amplifier via a resistors $R_2$ and $R_4$. A series of diodes act to clamp voltage between the resistors $R_3$ and $R_4$ and the DC amplifier. Diodes of the exemplary circuit 800 include $D_1$, $D_2$ and zener diode $D_Z$. Other arrangements may be suitable to achieve an appropriate signal indicative of one or more potentials or a potential difference(s). In the exemplary circuit 800, the DC amplifier can then amplify the difference in electrical potential between the electrode E_1 and the electrode E_2 as the electrodes interact with a conductive fluid. Also shown in FIG. 8 is a tap electrically connected to, for example, a ground of the exemplary circuit 800 and may be used as a reference with respect to the signal from the DC amplifier (see, e.g., "signal"). Such a signal may be input to an analog-to-digital converter or other circuitry to determine various conditions related to one or more leads, electrodes, etc.

Figure 9A:
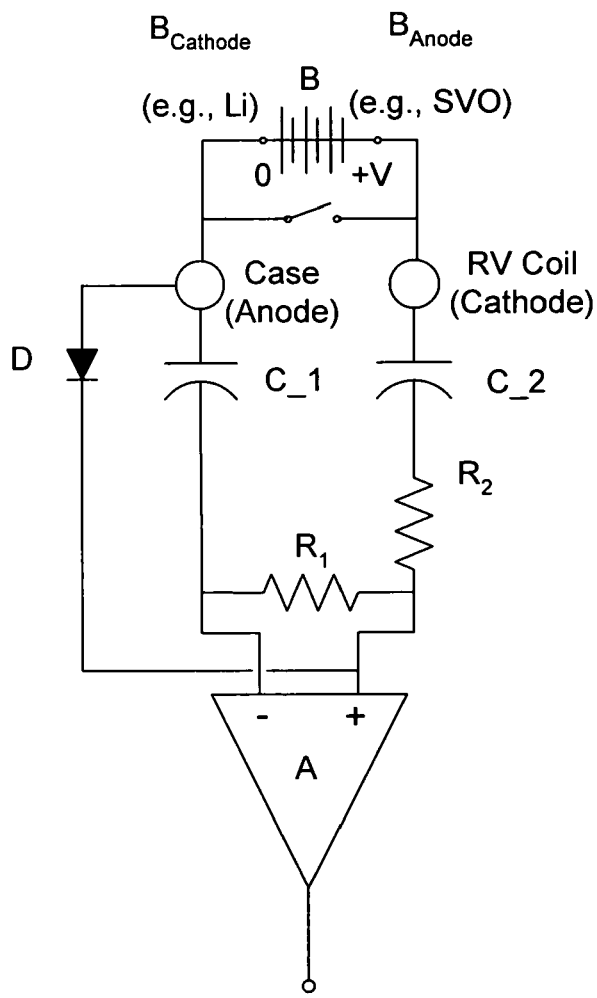
FIGS. 9A and 9B are schematics of two exemplary circuits capable of measuring one or more electrical potentials.
Figure 9B:
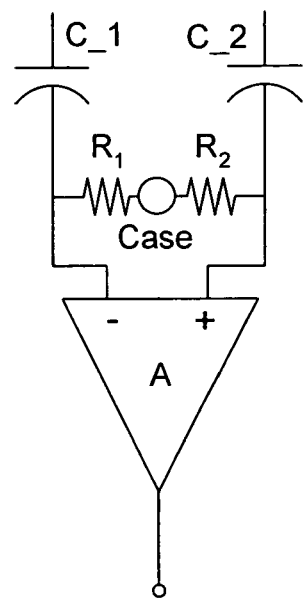

FIG. 9A shows an exemplary circuit 910 for sensing a potential that includes at least one half-cell potential and FIG. 9B shows another exemplary simplified circuit 920 for sensing a potential that includes at least one half-cell potential. The circuit 910 includes a battery, B, with a cathode, $B_{Cathode}$ (e.g., lithium), and an anode, $B_{Anode}$ (e.g., SVO). In this example, the battery has a potential of +V volts as measured between $B_{Cathode}$ and $B_{Anode}$ and a case electrode serves as an anode and a RV coil electrode serves as a cathode. An amplifier, A, acts to amplifier a difference in half-cell potentials between these two electrode. Positioned intermediate of the two electrodes and the amplifier are capacitors $C_{B1}$, $C_{B2}$, which act to remove slow DC electrode voltage fluctuations and reduce common mode rejection requirements of the amplifier. Positioned intermediate the capacitors and the amplifier are resistors $R_1$, $R_2$. A diode, D, positioned between the case electrode (anode) and an input (+) to the amplifier acts to limit any reverse current flow from the coil electrode (cathode) and the case electrode (anode).

The exemplary simplified circuit 920 shows the capacitors $C_{B1}$, $C_{B2}$, the case electrode, the resistors $R_1$, $R_2$ and amplifier A. Such a simplified circuit may be characterized by a time constant, τ, according to the following equation (Eqn. 1):

$$\tau = \frac{1}{2}\pi f \quad (1)$$

where f is the frequency. Assuming a frequency of approximately 1 Hz, such a circuit has a time constant of approximately 140 ms.

Figure 10:
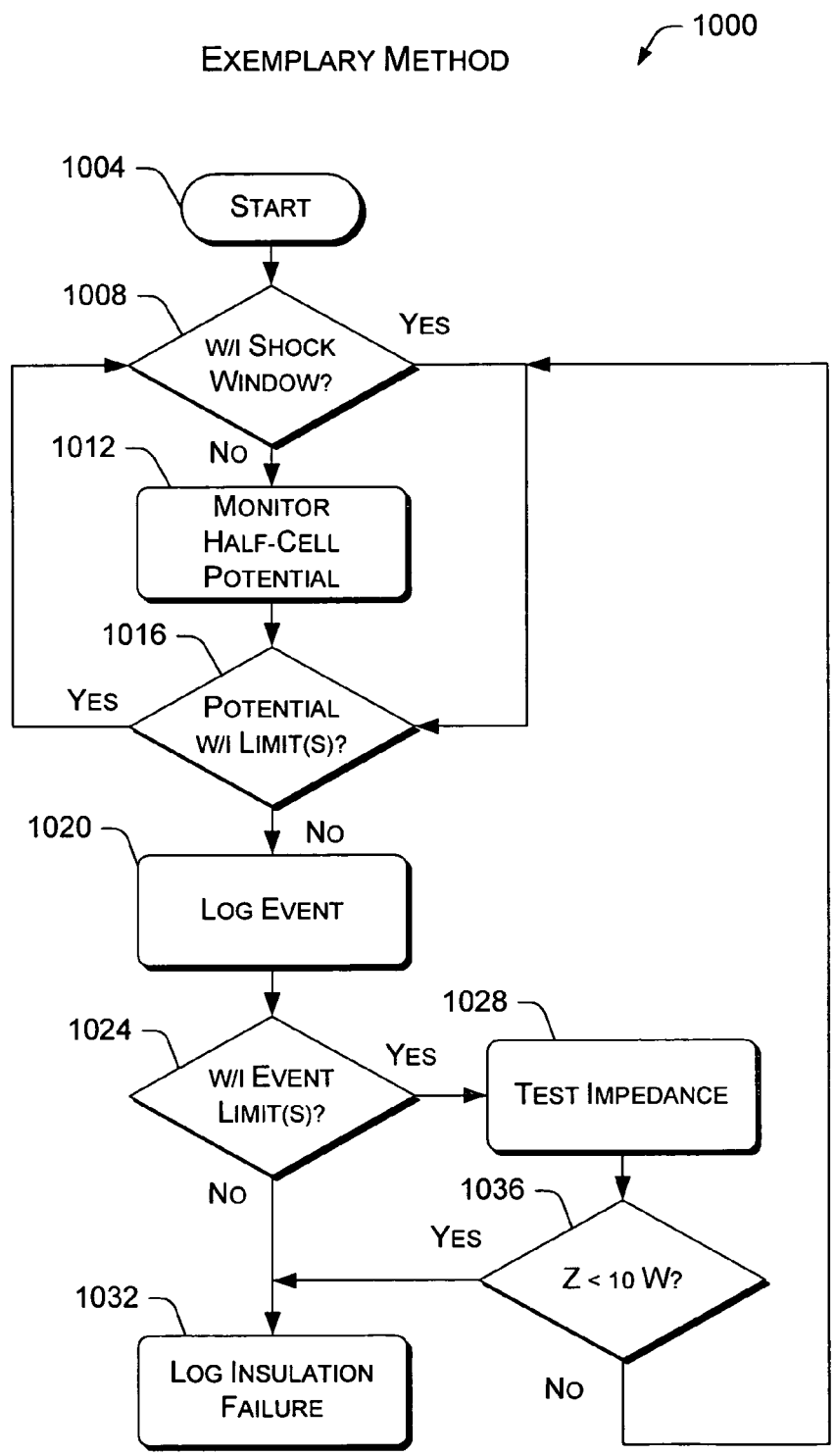
FIG. 10 is a block diagram of an exemplary method for implementing an exemplary mechanism such as the mechanism described with respect to FIG. 6.

FIG. 10 shows a block diagram of an exemplary method 1000 that relies on an exemplary mechanism for detecting insulation and/or impedance issues. The method 1000 commences in a start block 1004, which is optionally implemented on a periodic basis and/or in response to occurrence of one or more conditions. A decision block 1008 follows wherein a decision is made as to whether a timer indicates that a shock is imminent and/or that a shock has just been delivered. In general, a potential difference measurement circuit will not be able to provide adequate measurements of the potential difference during delivery of a shock or during a short period after delivery of a shock. In the former instance, the shock energy would typically overwhelm the measurement circuit while an aftershock period may include electrode after-polarization artifact that could corrupt measurement of a potential difference.

If the decision block 1008 decides that a shock is imminent or has been just delivered, then the method 1000 may enter a loop or a wait block within a loop that returns to the decision block 1008 after an appropriate wait. If the decision block 1008 decides that a shock is not imminent or has not been just delivered, then the method 1000 continues in a measurement block 1012. The measurement block 1012 measures one or more half-cell electrical potentials and/or a difference between two or more half-cell potentials. Another decision block 1016 follows that decides how the one or more measured half-cell electrical potentials compare to one or more corresponding limits. If the decision block 1016 decides that the measured values or difference values are within the one or more limits, then the method 1000 continues at the decision block 1008. However, if the decision block 1016 decides, for example, that a difference between two electrical potentials has fallen below a predetermined limit, then the method 1000 continues a log event block 1020.

The log event block 1020 acts to log the event, as appropriate. For example, the event may be logged using an event counter, an event duration, etc. A decision block 1024 compares such logged information to one or more limits to decide on subsequent action (e.g., time limits, event limits, etc.). For example, if a limit of 10 log events over a period of time, or since implant, is exceeded, then the method 1000 may proceed to a log insulation failure block 1032 wherein a marker notifies a care provider that an insulation failure occurred. The log block 1032 may also inhibit delivery of certain therapy or sensing or take other action. If the decision block 1024 decides that the logged information is within one or more limits, then the method 1000 may investigate the event further. For example, according to the exemplary method 1000, an impedance test block 1028 may test impedance and use this information in an impedance decision block 1036. The impedance decision block 1036 compares the impedance to a limit $Z_L$. If the impedance is less than the limit, then it is likely that an insulation failure has occurred and the method continues to the log insulation failure block 1032. However, if the impedance is equal to or greater than the limit, then the method 1000 continues to the decision block 1008. In this latter instance, a high impedance indicates that an insulation failure is unlikely based on the number of events, the duration of the event, etc.

Various exemplary methods, devices, systems, etc., include monitoring or are capable of monitoring lead integrity and/or insulation integrity on a substantially continuous basis, for example, where interference from or with other functions is not an issue. Such monitoring relies on measurement of one or more half-cell potentials for a metal and/or an alloy in the body. In particular, where an implantable device with one or more leads exposes two different metals and/or alloys to the body, a difference between the half-cell potentials for the different metals and/or alloys may be measured.

Where integrity of a lead and/or its insulation has not been compromised, a standard value may be determined as a half-cell potential or a potential difference. Should a change occur in integrity, then the half-cell potential or potential difference may be expected to change as well. Measurement of such a change at a moment in time and/or over a period of time can indicate lead condition.

An exemplary method includes measuring a potential difference between a platinum coil electrode (e.g., a defibrillation electrode, etc.) in a body and a titanium case electrode (e.g., case of a defibrillation device, etc.) in the body. While platinum and titanium are both cathodic, platinum is more so than titanium; hence, titanium would be anodic and a potential difference will exist between these metals in a body (e.g., consider a saline medium). If insulation of a lead bearing the platinum coil electrode shorted to the titanium case electrode (see, e.g., FIG. 3), then the potential difference will change. As already mentioned, lead insulation often contacts the case of a pulse generator and may wear and thereby expose the lead conductor to the case. Of course, a change in measured potential for the platinum coil electrode may be expected even when the lead conductor is exposed to body fluid and/or tissue and also if fracture of the conductor or other loss of connection to the circuitry of the case (e.g., generator circuitry) is compromised. Thus, such an exemplary method may be capable of detecting conductor fracture, insulation failure, etc.

In the preceding example, when the coil electrode is not in use (e.g., for delivery of a pulse), a continuous and substantially steady half-cell potential (e.g., substantially DC potential) will exist between the coil and the surrounding medium. In general, a coil electrode has a large surface area, which acts to diminish polarization associated with pulse delivery. Further, such a polarization artifact typically diminishes rapidly after pulse delivery.

CONCLUSION

Although exemplary mechanisms have been described in language specific to structural features and/or methodological acts, it is to be understood that the subject matter defined in the appended claims is not necessarily limited to the specific features or acts described.

What is claimed is:

1. A method comprising:
   determining a potential difference between a first half-cell potential associated with a first electrode composed of a first material in contact with a conductive fluid or tissue and a second half-cell potential associated with a second electrode composed of a second material in contact with a conductive fluid or tissue, wherein the second material is different from the first material; and
   altering a cardiac therapy if the difference falls below a predetermined limit.

2. The method of claim 1, wherein the first electrode comprises a coil electrode.

3. The method of claim 1, wherein the second electrode comprises a case electrode.

4. The method of claim 1, wherein the conductive fluid or tissue in contact with the first electrode comprises physiological fluid or physiological tissue and the conductive fluid or tissue in contact with the second electrode comprises physiological fluid or physiological tissue.

5. The method of claim 1, wherein the cardiac therapy comprises a therapy selected from the group consisting of sensing therapies, pacing therapies, stimulation therapies and shock therapies.

6. The method of claim 1, further comprising determining that a defect exists in insulation that insulates a conductor associated with the first electrode or the second electrode if the difference falls below a predetermined limit.

7. The method of claim 1, further comprising determining that a defect exists in a conductor connected to an electrode if the difference falls below a predetermined limit.

8. A method comprising:
   determining a half-cell potential associated with an electrode composed of a material in contact with a conductive fluid or tissue;
   altering a cardiac therapy if the half-cell potential falls below a predetermined limit; and further comprising
   determining that a defect exists in insulation that insulates a conductor associated with the electrode if the half-cell potential falls below a predetermined limit.

9. The method of claim 8, wherein the electrode comprises a coil electrode.

10. The method of claim 8, wherein the conductive fluid or tissue comprises physiological fluid or physiological tissue.

11. The method of claim 8, wherein the cardiac therapy comprises a therapy selected from the group consisting of sensing therapies, pacing therapies, stimulation therapies and shock therapies.

12. A method comprising:
   determining a half-cell potential associated with an electrode composed of a material in contact with a conductive fluid or tissue;
   altering a cardiac therapy if the half-cell potential falls below a predetermined limit; and
   further comprising determining that a defect exists in a conductor connected to an electrode if the half-cell potential falls below a predetermined limit.

* * * * *